United States Patent
Cracauer et al.

[11] Patent Number: 6,039,714
[45] Date of Patent: Mar. 21, 2000

[54] COLLAPSIBLE RETENTION BOLSTER FOR GASTROSTOMY AND OTHER OSTOMY TUBES

[75] Inventors: Raymond F. Cracauer, Plymouth; Lester D. Michels, Eden Prairie, both of Minn.

[73] Assignee: Novartis Nutrition AG, Berne, Switzerland

[21] Appl. No.: 09/076,443

[22] Filed: May 12, 1998

[51] Int. Cl.[7] .............................. A61M 5/32; A61M 11/00
[52] U.S. Cl. ........................ 604/174; 604/93; 604/500; 604/523
[58] Field of Search ............... 604/29, 93, 103–107, 604/174, 177, 178, 264, 523, 536, 500; 128/DIG. 26

[56] References Cited

U.S. PATENT DOCUMENTS

| | | | |
|---|---|---|---|
| 3,815,608 | 6/1974 | Spinosa et al. | 128/349 R |
| 4,301,815 | 11/1981 | Doring | 128/785 |
| 4,668,225 | 5/1987 | Russo et al. | 604/270 |
| 4,795,430 | 1/1989 | Quinn et al. | 604/97 |
| 4,863,438 | 9/1989 | Gauderer | 604/247 |
| 4,944,732 | 7/1990 | Russo | 604/247 |
| 5,073,166 | 12/1991 | Parks et al. | 604/93 |
| 5,125,897 | 6/1992 | Quinn et al. | 604/99 |
| 5,248,302 | 9/1993 | Patrick et al. | 604/178 |
| 5,391,159 | 2/1995 | Hirsch et al. | 604/268 |
| 5,413,565 | 5/1995 | Michels et al. | 604/247 |
| 5,556,385 | 9/1996 | Anderson | 604/174 |
| 5,857,999 | 1/1999 | Quick et al. | 604/107 |

OTHER PUBLICATIONS

Corpak, Inc., The Bower P.E.G. System, Unique collapsible retention balloon means easier, safer insertion—and removal without endoscopic retrieval; Literature, no date.
Bard Guidewire P.E.G. System with Soft Silicone Retention Dome—Instructions For Use, Literature, no date.
Bard, Ponsky "Pull" P.E.G. Tray with Soft Silicone Retention Dome—Instructions For Use; Literature, no date.
BioSearch Medical Products, Inc., Dobbhoff Single Pass P.E.G. (Allows Single Endoscopic Insertions) featuring the "Patient Comfort Removal System", Literature, no date.

*Primary Examiner*—Corrine McDermott
*Assistant Examiner*—Michael J. Hayes
*Attorney, Agent, or Firm*—Michael P. Morris

[57] ABSTRACT

The present invention is an improved ostomy fluid tube and method for its use comprising a collapsible retention bolster for securing the tube to the inner stomach wall and fascia. The retention means comprise several resilient leaf or petal-shaped flanges circumferentially arranged about the feeding tube at a distal point thereon. The otherwise flat, circumferentially arranged flanges possess notches or grooves which facilitate collapse or folding of the retention means for easier removal through an ostomy or other internal cavity.

26 Claims, 2 Drawing Sheets ial implantation and use.
COLLAPSIBLE RETENTION BOLSTER FOR GASTROSTOMY AND OTHER OSTOMY TUBES

FIELD OF THE INVENTION

The present invention relates generally to tubes for use in surgically incised ostomies for the transport of fluids therethrough. Specifically, the invention relates to enteral feeding devices and methods for their surgical implantation and use. More specifically, the present invention relates to improvements in these devices for the placement and retention of gastrostomy and jejunal feeding tubes.

BACKGROUND OF THE INVENTION

There are many patients affected with disease or other physiological conditions that result in the inability to receive nutrition normally through the mouth which is then swallowed and broken down and absorbed by the digestive system. People suffering from stroke, Alzheimer's disease, cancer, inflammation or other infirmities, often cannot properly chew or swallow their food or medication which must then be delivered to the patient in another fashion if starvation and malnutrition are to be avoided.

Gastroenterologic feeding tubes have been known for years and are inserted into the stomach by any one of a number of different methods. Generally, a catheter is placed in the body by way of the mouth and is either pulled or pushed downward into the stomach and either left there or is pushed further down into the jejunum of the small intestine. The feeding tubes may also enter the body either by way of the nasal passageway or by means of a gastrostomy in which they are surgically implanted through the abdomen.

The present invention relates to the enteral feeding of patients by these tubes and more particularly to a gastrostomy or jejunal feeding tube which is receivable through the wall of the stomach for feeding and medicating a patient and/or for draining fluids from the patient's stomach. The present invention also relates a jejunostomy tube which similarly is receivable into the small intestine from outside the patient's abdomen.

The use of feeding tubes which extend directly into the stomachs of patients is often required when patients cannot swallow or when they have structures in their esophagi which prevent food from entering their stomachs. In a situation of this type, it is common to perform a gastrostomy on a patient wherein an opening is formed in the skin, facia and stomach wall and wherein a gastrostomy tube is installed in the opening to allow food and/or medication to be passed directly into the stomach and also to allow fluid to be drained therefrom.

Enteral feeding tubes that enter the stomach through a surgically incised opening through the skin, facia and peritoneum must be secured in some manner so that the tube does not move about within the patient or fall out altogether if pulled. Generally, enteral or gastrostomy feeding tubes are either surgically inserted through the skin of the abdomen or fed down to the stomach by way of the mouth and pharynx.

Various types of gastrostomy devices have been installed in patients by means of a percutaneous insertion, a surgical placement, a radiological placement or others. The procedures employed generally follow those known as the Sachs-Vine procedure, the Gauderer and Ponsky procedure, and others. Typical patents describing these procedures and publications of the technique are set forth in U.S. Pat. Nos. 4,861,334 to Nawaz 4,900,306 to Quinn et al. and 5,080,650 to Hirsch et al. which are hereby incorporated by reference.

Once installed, these devices are retained in place by an internal retention member. Various types of these internal retention members currently exist, one type being a molded or permanently attached flange element, and another type being a bumper collar and a third type being a balloon.

Removal of gastrostomy devices is needed upon conclusion of enteral nutrition of a patient, or if the device is to be replaced with another enteral feeding device (e.g., an inflatable, replaceable gastrostomy tube), and various techniques are currently used for this removal procedure. These techniques include (1) cutting the gastrostomy tube at skin level and retrieving the bumper endoscopically; (2) cutting the gastrostomy tube past skin level and allowing the flange or collar to pass through the gastrointestinal tract for expulsion by excretion; or (3) physically pulling the internal retention device through the patient's stoma.

Problems exist with the methods known in the prior art particularly with respect to the removal of the retention means through the surgical incision when enteral feeding or medication is concluded. Since the retention means must generally possess an extended surface area or circumference that is greater than the tube itself, movement of this portion of the device can result in tissue damage and/or irritation as the enteral feeding tube is pulled through the esophagus, stomach, intestines and/or the surgical incision. This can result in considerable trauma and/or bleeding within the patient.

There have been a number of attempts in the prior art which have addressed, but not necessarily solved this problem. U.S. Pat. No. 5,336,391 to Stewart discloses a gastrostomy feeding tube with a flexible retainer that consists essentially of a dome or cup-shaped flange is allegedly designed to collapse significantly in diameter when a force is applied longitudinally along the central axis of the enteral feeding tube. The collapsing function of this placement dome is asserted to allow for the easier passage of the retention means during either placement or removal of the gastrostomy feeding tube.

U.S. Pat. No. 5,112,310 to Grobe discloses a percutaneous gastrostomy feeding tube in which the retention means consists of a collapsible basket-shaped device including a plurality of elongated flexible or deformable, but relatively stiff ribs circumferentially spaced one from the other. The ribs are secured at one end to a collar that is fixed to the feeding tube and at the opposite end the ribs are attached to a collar that is slidably attached to the tube. Movement of the slidable collar when force is applied to the basket from the opposite side ostensibly deforms or collapses the basket thereby narrowing its diameter so that the tube may be moved within or withdrawn from the patient's body.

U.S. Pat. No. 5,098,378 to Piontek et al. discloses and claims a replacement gastrostomy tube for jejunal feeding in which an expandable component of the tube is located at the distal end thereof. Fluid is passed through a fluid flow channel which enters the expandable component and inflates it like a balloon. In this fashion, the balloon and an adjacent retention device are pressed against the wall of the stomach, securing the feeding tube in the stoma. Draining the fluid from the balloon deflates it for easier removal.

U.S. Pat. No. 4,668,225 to Russo et al. discloses and claims an enteral gastrostomy feeding tube comprising a retainer element consisting of a plurality of circumferentially spaced resilient leaves or flanges with a rounded configuration that extend outwardly from the feeding tube.

The retention means also consists of three hub portions which extend outwardly to a lesser extent between the leaves. The "petals" or "leaves" of the retainer element engage the inner surface of the stomach wall with the feeding tube passing centrally therethrough. These would appear to cause considerable abrasion upon removal however.

None of these prior art feeding tubes and their associated retention means provide a superior means for securing the feeding tube to the interior wall of the stomach with a rigid mounting while at the same time being flexible enough to collapse upon applying a lateral force thereto so as to readily and easily pass through a surgical ostomy or other internal cavity without damaging the surrounding tissue.

SUMMARY OF THE INVENTION

The present invention is directed to an improved retention bolster for securing a tube to an ostomy such as urinary catheters, intraperitoneal catheters, gastrostomy tubes, jejunal tubes and the like. Preferably, the present invention comprises an improved gastroenterologic feeding tube and method for its use comprising a collapsible retention bolster for securing the tube to the digestive tract wall, in particular the inner stomach or jejunal wall and fascia. The retention bolster is comprised of several resilient leaf or petal-shaped flanges circumferentially arranged about the feeding tube at a distal point thereon. The otherwise flat, circumferentially-arranged flanges possess notches or grooves which facilitate collapse or folding of the retention bolster for easier removal through the associated ostomy or up through the trachea and mouth.

DETAILED DESCRIPTION OF THE INVENTION

Figure 3:
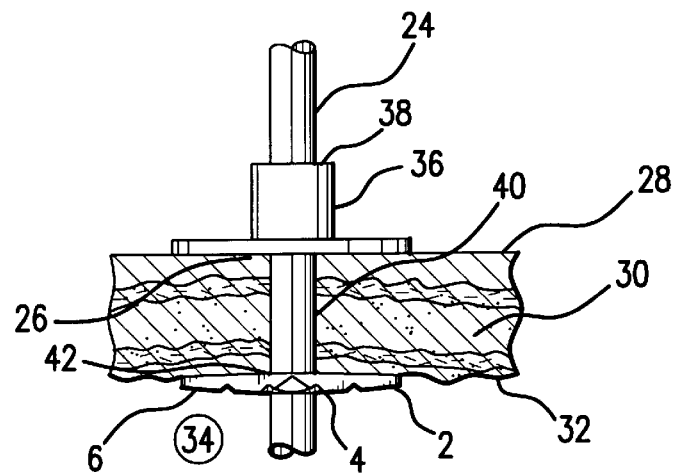
FIG. 3 is a traverse side view of a patient's stomach wall and fascia with a gastroenterologic feeding tube inserted therein.

The ostomy feeding tubes of the present invention is in many respects essentially configured similar to those of the prior art and positioned within the patient so that it extends through the peritoneum, fascia and skin. These may comprise standard urinary catheters, intraperitoneal catheters, gastrostomy feeding tubes, jejunal feeding tubes, colonostomy and ileostomy tubes and the like. The improved retention means of the present invention engages the inner surface of the body cavity as is seen in FIG. 3 which depicts its use in a gastrostomy feeding tube. In this manner, the distal end of the tube empties into the stomach lumen.

When used with a gastrostomy or jejunal feeding tube, the tube also contains a connecting element at the proximate end thereof for the attachment of a nutrition or medicinal source as is known in the art. This may be comprised of a single port if only one type of fluid is fed to the patient or two or more ports if more than one type of fluid is to be administered simultaneously. As noted above, some gastrostomy tubes which are placed either surgically or endoscopically may be removed using external traction such that the internal (gastric) retainer or bolster collapses into the stoma tract and the tube is extracted through the tract. The design intention of such devices is that the internal bolster has sufficient resilience to maintain tube position within the stomach, but will collapse under a given amount of tension and will pass through the stoma tract without damaging the surrounding tissue. The design of the retainer means of the present invention, however, affords the advantage that while the retention force that exists when the retainer is secured to the inner stomach wall is the same if not greater than the retention means known in the prior art, the force required to remove the feeding tube from the patient through the ostomy is much less resulting in less chance for damage and trauma to the surrounding tissue.

Figure 1:
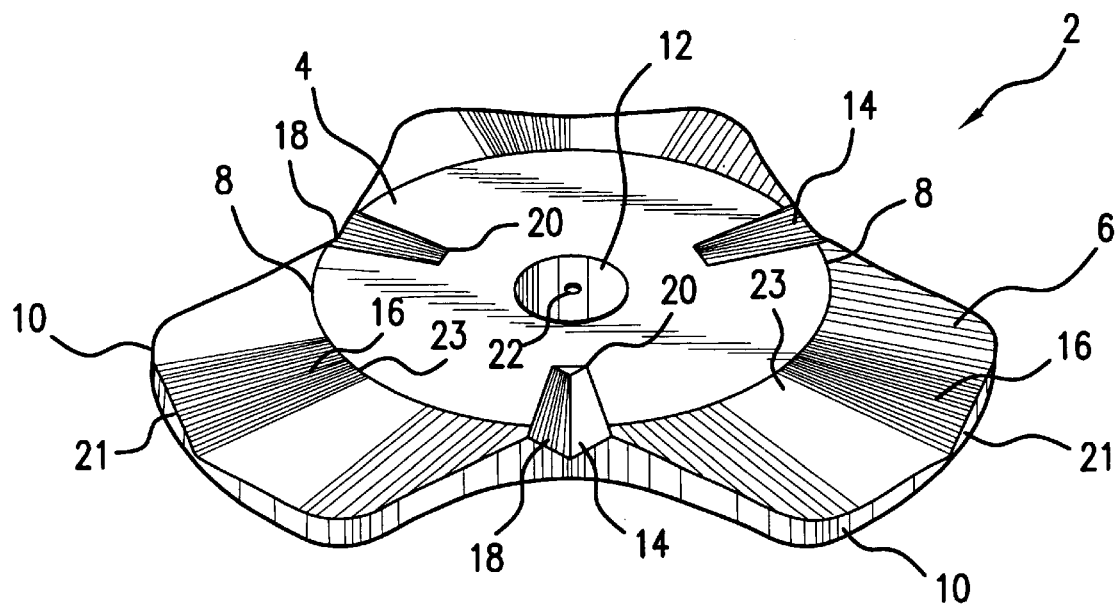
FIG. 1 is the flexible retention bolster of the present invention.

Referring now to FIG. 1, the improved collapsible retainer bolster (2) is shown alone, apart from the standard gastrostomy tube with which it would otherwise be associated. The gastrostomy retainer bolster is comprised of a substantially circular central base portion (4) from which plural flanges or leaves (6) extend outwardly from the central circular core (4). Preferably, the leaves or flanges are substantially equidistantly arranged about the central core. The leaves or flanges (6) are preferably similar, or more preferably identical in their shape and design and the proximate portions thereof (8) that are congruent to and/or a part of the periphery of central core base (4) encompass substantially the entire circumference or periphery of the core portion (4). Preferably, the bolster comprises three or more leaves or flanges (6). The width of the leaves preferably is slightly tapered from their proximate end (8) to their distal end (10) and the thickness of the leaves is also preferably tapered from the proximate (8) to the distal end (10). The preferred tapering of the thickness of the leaves (6) is such that the proximate end is essentially the same thickness as the central core (4) which then lessens to the distal end. For example, the distal end (10) may be from about three fourths (¾) to as little as one-tenth (¹⁄₁₀) or less that of the proximate end.

As is also evident from FIG. 1, the central base portion (4) also has a centrally located bore (12) that extends throughout the central base for the passage of the gastroenterologic feeding tube, (not shown). Since the retention bolster (2) of the present invention can be manufactured in any number of different sizes according to the size of the associated tube, the size of the central bore will be such that the associated tube will fit snugly therein. The bolster retention means (2) may be molded as a part of the outer circumference of the feeding tube or the tube may be separate from and slideably inserted therein such that the retention bolster is able to be moved along the surface of the tube. If this is the design, the size of the central bore will be such that the associated tube will fit snugly therein so that the retention bolster is not easily moved. The bolster retention means (2) should be able to move along the surface of the tube as it is pulled or pushed through the central bore (12) but not without some frictional resistance. Again, the degree of resistance is dictated by the size of the bore (12) which is also determined by the circumference of the tube with which it becomes functionally associated. In either case, the fit should not be such that the gastrostomy tube is "pinched" when positioned within the bore. The retention bolster may also be formed as an integral element of the tube and immovably fastened thereto.

The preferred embodiment of the collapsible retention bolster (2) of the present invention as shown in FIG. 1 is further comprised of two sets of cut-away wedges or grooves within the central circular base (4) and flanges (6), respectively. The first set of grooves (14) are substantially equidistantly disposed within the circular base (4) at approximately 120 degree intervals. As can be seen from FIG. 1, the grooves or wedges are v-shaped and extend somewhat more than half the length of the radius of the circular base (4). As is also apparent from FIG. 1, the wedges are tapered such that the width of the groove at the distal end (18) of the base (4) is greater than the width at the proximal end (20). However, the widths and depths could vary in both size and shape and could be both smaller or larger at the distal end then the proximal end. In addition, whereas the grooves are of a v-shaped design in the Figure, they need not be limited to this shape and could ultimately be in other shapes, for example rectangular-shaped or even narrow slits. Whereas the wedges may vary in size, preferably they are cut into the circular base (4) to a depth of about ¼ to ⁹⁄₁₀ or more the entire thickness of the base.

The second set of wedges or grooves (16) are formed within the flexible leaves or flanges (6) that outwardly extend from the circular base (4). As can be seen again from FIG. 1, the second set of grooves (16) are also tapered such that the width of the groove at the distal end (21) is wider than that at the proximal end (23). Although the depth of these grooves again may vary, generally they are formed within the flange (6) to a depth of from approximately one-quarter (¼) to about nine tenths (⁹⁄₁₀) or more the thickness of the flange. The proportionality of wedge depth/flange thickness preferably remains constant so that as the thickness of the flexible flange decreases moving outwardly from the circular base (4), so does the actual depth of the v-shaped wedge (16) even though the width of the wedge becomes greater. Again, as with the first set of grooves in the circular base, these grooves or wedges may vary in shape, depth, size and are not necessarily limited to the depictions in the drawings although these embodiments are preferred.

The grooves (14, 16) formed in the circular base (4) and flanges (6), respectively, impart increased flexibility and hence "foldability" of the retention bolster (2) of the present invention. As will be described in greater detail below, the expanding tapered design of both the circular base grooves (14) and the v-shaped wedges (16) provide increased flexibility to those areas of the circular base (4) and the outwardly radiating flanges (6) with increasing distance from the central axis (22) of the central bore (12). Logically, this is necessary because when lateral force is exerted in the direction of the central axis (22) of the retention bolster (2) such as when the gastrostomy tube is being inserted and pulled through the lining of the esophagus and stomach or is being removed and pulled out of the ostomy, those points furthest from the center of the retention bolster offer the greatest surface area and resistance so as to possibly result in abrasion and injury to soft tissue. The tapered wedge design in both the wedges (14) of the circular base (4) and the v-shaped grooves (16) of the outwardly extending flanges (6) increases the flexibility and collapsible nature of those portions of the retention means which are farthest removed from the center. This results in a surprisingly and unexpected foldable and collapsible retention bolster that offers far less resistance to force when pulled and therefore creates far less tissue irritation or damage as the gastrostomy feeding tube is pulled through a patient Yet, the overall size of the flanges (6) and the central circular base (4) affords a secure hold upon the lining of the stomach wall to maintain the feeding tube in place when inserted and operational within the patient. In other words, the retention force of the bolster retainer is improved while positioned in the stomach yet the force needed to be applied for removal is substantially reduced.

Figure 2:
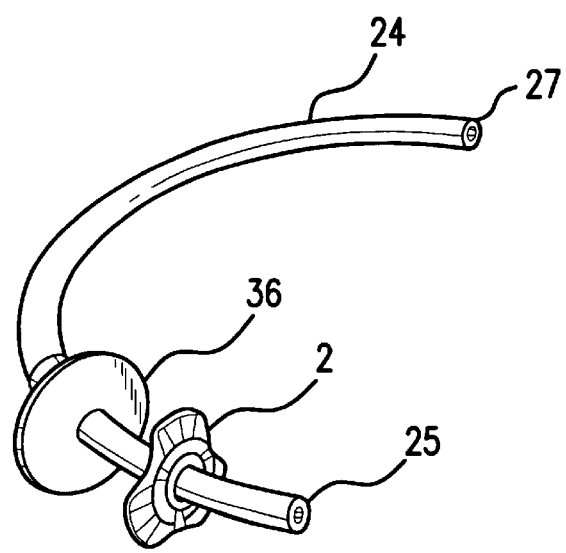
FIG. 2 is an overall view of a Gastroenterologic feeding tube including the improved retention bolster of the present invention.

Referring now to FIG. 2, the retention bolster (2) is shown in association with the ostomy tube (24) and an external retention bolster (36) which secures the tube to the skin of the patient when in use. The proximal end of the tube (25) feeds into the stomach, small intestine or other target body cavity while the distal end (27) generally leads to feed ports (not shown) or, if used as a drainage means, disposal bags and the like.

As briefly discussed above, the collapsible bolster of the present invention may either be slideably inserted over the surface of a standard gastrostomy tube providing there is a certain tightness or resistance to prevent easy movement thereover or it may be formed as an integral part thereof Preferably, the collapsible retainer bolster will be made from the same flexible non-toxic materials as the gastrostomy tubes such as biocompatible polymers, including silicone rubber, silicone elastomers, polyurethane, silicone copolymers, polypropylene and/or other similar materials or combinations thereof typically used in the art.

Referring now to FIG. 3, the improved retention bolster of the present invention is shown secured to the stomach wall of a patient as a part of the gastrostomy feeding tube with which it is used. The tube itself (24) enters the ostomy (26) surgically incised within the patient's skin (28) through the muscle fascia (30), the mucosal lining (32) and into the stomach cavity itself (34). The central base portion (4) and the collapsible flanges or leaves (6) are maintained flush with the inner lining of the stomach mucosa. An external, rigid bolster portion (36) is maintained outside the body flush with the skin (28) as is known in the art. The external bolster (36) also has a central cavity or bore (38) so that the tube portion (24) may pass therethrough. Aligned and congruent with this central bore is a second section of the feeding tube (40) which is the portion that actually enters and passes through the skin (28) and stomach mucosa (32).

This shorter segment of the gastroenterology feeding tube (40) is also attached at its proximal end (42) to the central bore (12) of the gastroenterologic retention bolster device of the present invention. In another alternative embodiment, the tube (24) may comprise one long unitary piece of tubing that is not attached to the external (36) and internal (2) gastroenterologic bolsters but merely passes through each of their central bores (22 and 38, respectively) and then into the stomach. In this embodiment, the central piece of tubing (40) will not be separate but merely a part of the greater whole of the tube.

As can be further seen from FIG. 3, the surface area of the internal retention bolster (2) is greatly enhanced by the flexible flanges (6) or leaves which lie flat against the stomach lining of the patient (32). The first set of v-shaped grooves (14) can be seen positioned within the circular base (4) at equidistant intervals about its periphery. The second set of wedges or grooves (14) which impart the enhanced flexibility and hence, collapsibility of the flanges (16) can also be seen herein. The collapsible bolster is retained against the stomach lining in this manner yet is easily removable by turning the feeding tube (24) in a counter-clockwise direction as is known in the art.

A major advantage of the collapsible retention bolster of the present invention is the ability to remove it without the need for endoscopy. To this end, the jejunal feeding tube (if present) and feeding adapter are removed from the external bolster (36) on the skin surface. The remaining outlet tube (24) is typically lubricated and rotated within the stoma, thereby drawing lubrication into the tract. The physician then presses down on the abdomen around the tube while at the same time pulling the tube out and away from the abdomen. The leaves or flanges (6) of the retention bolster will slowly fold and the tube with the bolster will "pop" out.

Whereas some force is required to bend the leaves (6) outward from their center axis so as to pull the bolster through the stoma, much less is required to fold them inwards as the retention means is pulled out of the ostomy or down through the esophagus, epigastric sphincter and into the stomach. Again, this prevents injury to the surrounding delicate tissues and facilitates tube insertion, placement and removal.

Figure 4:
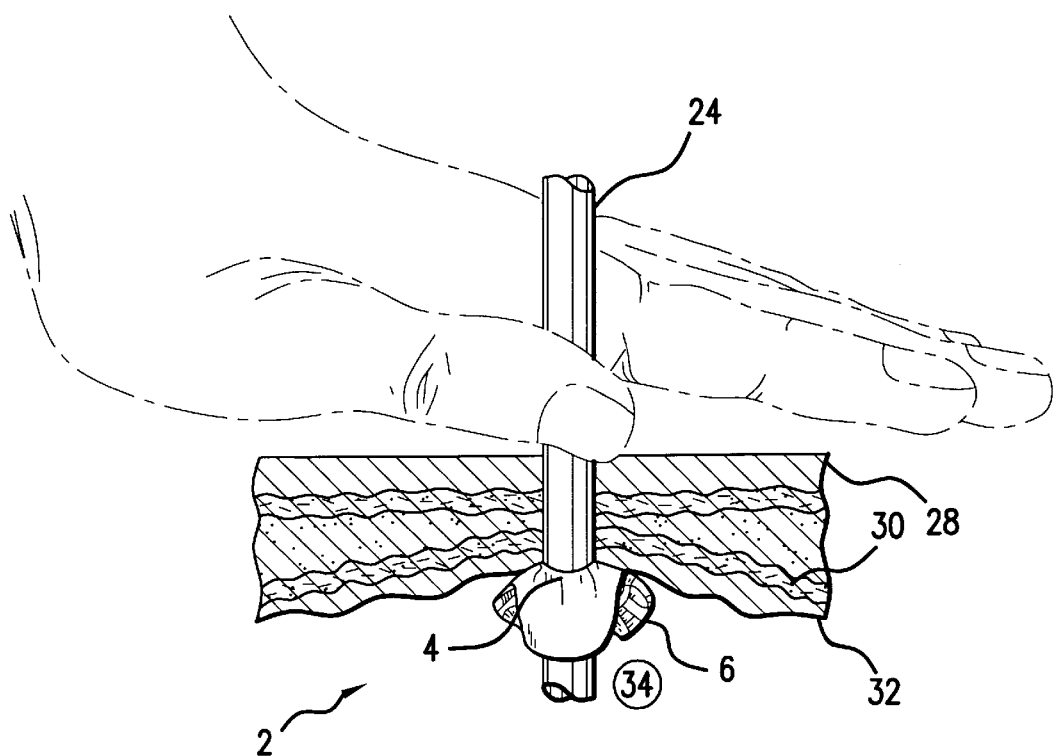
FIG. 4 is a transverse side view of the retention bolster being removed from the patient's stomach.

Referring now to FIG. 4, the collapsible retention bolster (2) is shown in association with the gastrostomy tube as it is being withdrawn from the patient in its collapsed state through the ostomy. As can be seen from the drawing, both the flexible leaves (6) and the central circular base portion (4) bend when lateral force is exerted against them as exhibited by arrow A when frictionally pulled along the surface of the mucosa. In this collapsed state, little pressure or friction is exerted by the edges of the bolster retention means so as to possibly result in tearing, injury or trauma to the stoma or ostomy tract.

It should be understood that the disclosure set forth herein and the accompanying drawings are merely suggested embodiments of the present invention and it is recognized that minor changes and variations can be made thereto that are not specifically disclosed. It should be understood that to the extent any such changes do not materially change or alter the design or functionality of the device, they are to be considered as falling within the spirit and scope of the invention as recited in the claims that follow.

What is claimed is:

1. A collapsible retention bolster for securing an ostomy tube to the inner wall of a body cavity lining of a patient comprising:
    a. a central circular base extending outwardly from a central bore with two or more radially disposed, spaced grooves cut therein; and
    b. two or more flexible flanges that are grooved along their central axis and extend outwardly from said base portion spaced about the periphery thereof and from between the grooves in said base.

2. The collapsible retention bolster of claim 1 wherein said ostomy tube is selected from the group consisting of gastrostomy feeding tubes, jejunal feeding tubes, colonostomy tubes, ileostomy tubes, gallbladder tubes, urinary catheters, intraperitoneal catheters and the like.

3. The collapsible retention bolster of claim 2 wherein said grooves are placed substantially equidistantly within said circular base.

4. The collapsible retention bolster of claim 3 wherein said grooves are v-shaped.

5. The collapsible retention bolster of claim 4 wherein said flexible flanges are tapered.

6. The collapsible retention bolster of claim 5 wherein said grooves of said tapered flanges are wider at the distal end of the flange than at the end proximate to the central circular base.

7. The collapsible retention bolster of claim 6 wherein the center of said central circular base portion is a substantially circular opening or bore passing therethrough for insertion of and attachment to said ostomy tube.

8. The collapsible retention bolster of claim 7 wherein said flexible flanges are tapered such that the thickness of each flange is greater at the proximal end wherein it is joined to or a part of the periphery of said central circular base than the thickness of the distal end of each flange that is the point farthest removed from said base.

9. The collapsible retention bolster of claim which is capable of engaging a gastrostomy tube on one side of the central base portion and is confluent with said central bore.

10. The collapsible retention bolster of claim 9 wherein said gastrostomy tube attaches to said bolster on each side of the tube at the central base and is confluent with said central bore.

11. A device for securing an ostomy tube to the outer skin and inner wall of a body cavity of a patient comprising an external and internal member wherein the external member comprises a stopping means for placement against the outer skin, and an internal member comprising the collapsible retention bolster of claim 1.

12. A method for securing a gastrostomy feeding tube to the abdomen and stomach of a patient comprising passing said tube through the central bore of the retention bolster of claim 1, surgically incising an opening in the skin, fascia and stomach mucosa of said patient, pulling said tube down through the esophagus and digestive system to a point wherein said retention bolster is flush with the stomach lining and passing the portion of said tube that is external to the patient's body through a second, rigid retention bolster that is positioned flush onto the outer skin of said patient.

13. An improved gastrostomy or jejunal feeding tube for the nutritional or medicinal treatment of a patient, said improvement comprising a collapsible retention bolster with two or more flexible flanges extending radially from a central circular base extending outwardly from a central bore, which flanges are tapered across the width and grooved for securing said tube to the inner lining or mucosa of the patient's stomach or intestine.

14. A collapsible retention bolster for securing an gastrostomy or jejunal feeding tube to the abdomen and lining of a patient comprising:
    a. a central circular base portion with at least two equidistantly spaced grooves cut therein; and
    b. at least two tapered flexible flanges extending from said base portion equidistantly spaced about the periphery thereof and extending from between each of the grooves in said base.

15. The collapsible retention bolster of claim 14 wherein said equidistantly spaced grooves cut within said circular base are v-shaped.

16. The collapsible retention bolster of claim 15 wherein said tapered flanges are also grooved along their central axis.

17. The collapsible retention bolster of claim 16 wherein said grooves of said tapered flanges are wider at the distal end of the flange than at the end proximate to the central circular base.

18. The collapsible retention bolster of claim 17 wherein the center of said central circular base portion is a substantially circular opening or bore passing therethrough for insertion of and attachment to said gastrostomy feeding tube.

19. The collapsible retention bolster of claim 18 wherein said flexible flanges are tapered such that the thickness of each flange is greater at the proximal end wherein it is joined to or a part of the periphery of said central circular base than the thickness of the distal end of each flange that is the point farthest removed from said base.

20. The collapsible retention bolster of claim 19 which is capable of engaging a gastrostomy of jejunal tube on one side of the central base portion and is confluent with said central bore.

21. The collapsible retention bolster of claim 20 wherein said gastrostomy tube attaches to said bolster on each side of the tube at the central base and is confluent with said central bore.

22. The gastrostomy feeding tube of claim 21 wherein said tube is easily withdrawn from the patient through an ostomy by pulling the tube and its retention bolster which results in the collapse of the retention bolster and substantially reduces the surface area and diameter thereof.

23. The gastrostomy feeding tube of claim 22 wherein said reduction in the surface area and diameter of the retention bolster is a result in the lateral collapsing and/or folding of a circular central base and equidistantly arranged flanges radiating therefrom that comprise the retention bolster.

24. The gastrostomy feeding tube of claim 23 wherein said tube is adapted to be secured to the abdomen and stomach of a patient by positioning a rigid, substantially circular retention basket externally onto the skin of said patient, passing said tube therethrough and securing it to the inner wall or stomach of the patient using the collapsible retention bolster.

25. The gastrostomy feeding tube of claim 24 wherein said central base and said flanges are grooved.

26. The gastrostomy feeding tube of claim 25 wherein said grooves are v-shaped and are wider at their distal end than at their proximate end.

* * * * *